United States Patent [19]

Durette

[11] 4,384,998
[45] May 24, 1983

[54] SYNTHESIS OF THIENAMYCIN FROM D-GLUCOSE

[75] Inventor: Philippe L. Durette, New Providence, N.J.

[73] Assignee: Merck & Co., Inc., Rahway, N.J.

[21] Appl. No.: 248,177

[22] Filed: Mar. 30, 1981

[51] Int. Cl.³ .................. C07D 205/08; C07D 487/04
[52] U.S. Cl. .......................... 260/239 A; 260/245.2 T; 260/349; 260/330.3; 549/22; 536/4.1; 536/122; 560/153
[58] Field of Search .................................. 260/239 A

[56] References Cited

U.S. PATENT DOCUMENTS 4,234,596 6/1980 Christensen et al. ........ 260/245.2 T

FOREIGN PATENT DOCUMENTS 7973 2/1980 European Pat. Off. .

OTHER PUBLICATIONS

S. Hanessian and R. Fords, Abst. Papers, 181st ACS National Meeting, CARB 27(1981).

Primary Examiner—Mark L. Berch
Attorney, Agent, or Firm—James A. Arno; Hesna J. Pfeiffer; Daniel T. Szura

[57] ABSTRACT

Disclosed is a chiral, total synthesis of thienamycin from D-glucose which proceeds via intermediates I, II and III to known aldehyde IV which is known to be useful in the total synthesis of thienamycin (V):

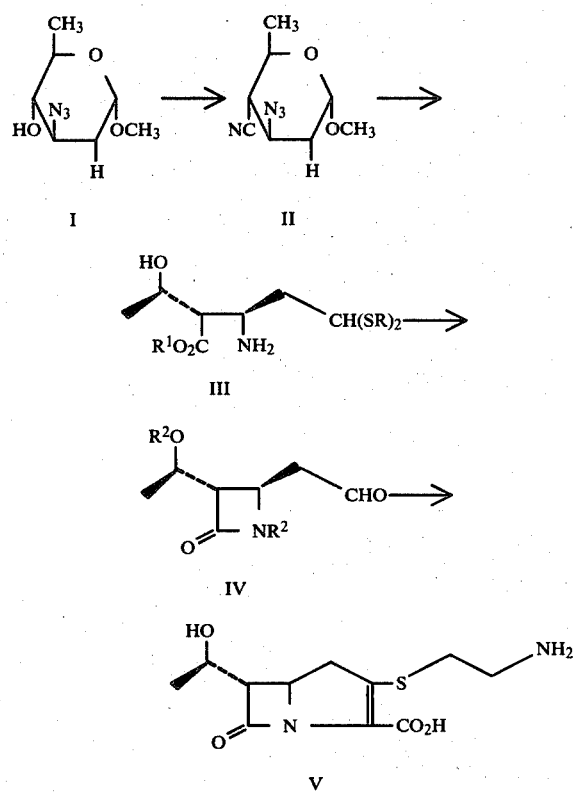

wherein: R is lower alkyl having 1–6 carbon atoms or bi-valent alkyl having 2–6 carbon atoms which joins the two sulfur atoms; $R^1$ is lower alkyl or aralkyl, such as benzyl and the like; and $R^2$ is hydrogen or a removable protecting group, such as triorganosilyl wherein the organo groups are independently selected from lower alkyl, phenyl and phenylloweralkyl.

2 Claims, No Drawings

SYNTHESIS OF THIENAMYCIN FROM D-GLUCOSE

BACKGROUND OF THE INVENTION

This invention relates to the chiral, total synthesis of thienamycin from D-glucose (dextrose).

In its broadest terms, the process proceeds from glucose via intermediates I, II, and III and encounters aldehyde IV which is known to be useful in the total synthesis of thienamycin (V).

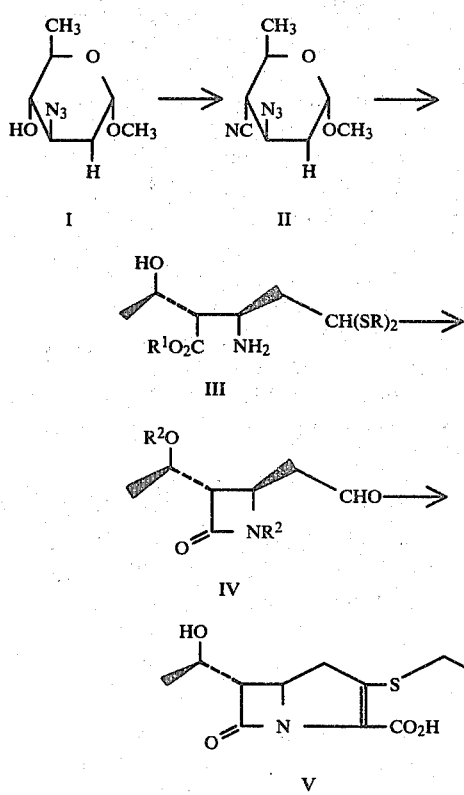

wherein: $R^2$ is hydrogen or a removable protecting group such as a triorganosilyl group wherein the organo moieties are independently selected from alkyl having 1–6 carbon atoms, phenyl, and aralkyl having 7–14 carbon atoms; $R^1$ is a lower alkyl having 1–6 carbon atoms, or aralkyl, for example, methyl, ethyl, propyl, benzyl, and the like; R is lower alkyl or the two sulfur atoms may be joined to form a ring comprising R.

The transformation IV→V is known. See, for example, U.S. Patent application Ser. No. 112,058 filed Jan. 14, 1980. To the extent that the cited U.S. Patent application discloses the utility of intermediate species IV and its transformation to thienamycin, it is hereby incorporated by reference. Also incorporated by reference for the same purpose are U.S. Pat. No. 4,234,596 (issued 11/18/80); and EPO application No. 79101307.1 filed 5-1-79, Publication No. 0007973.

Also incorporated by reference are the following concurrently filed, commonly assigned U.S. Patent applications of Philippe L. Durette Ser. Nos. 248,175, 248,178 now U.S. Pat. No. 4,348,325, 248,176 now U.S. Pat. No. 4,324,900, 248,174, (all filed Mar. 30, 1981). All of these applications relate to the synthesis of thienamycin from D-glucose.

As will be made evident from the Detailed Description of the Invention which follows, the presently disclosed and claimed process is characterized by several advantages. Most noteworthy is that the starting reagents for the process are inexpensive and safe to handle. The process is characterized by being conducted under moderate conditions which are amenable to scale up and by a sequence of steps which are individually high yielding. It should be further noted that in many of the sequences the intermediates need not be isolated so that individual sequences or distinct process steps may be conducted in a single pot.

DETAILED DESCRIPTION OF THE INVENTION

The process of the present invention may conveniently be represented by the following reaction diagram:

DIAGRAM I

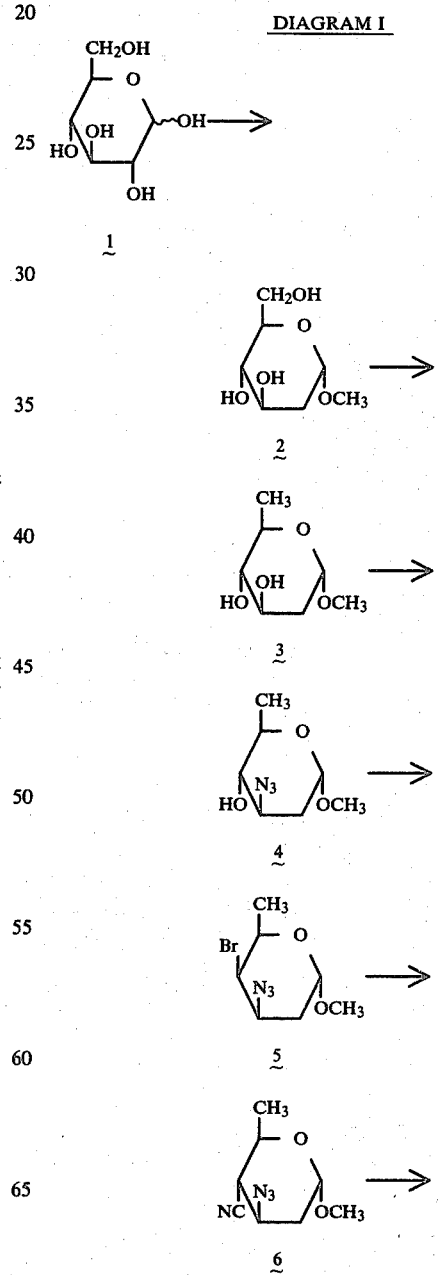

-continued
DIAGRAM I

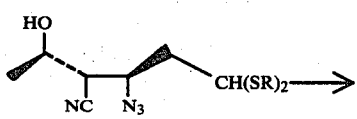
7

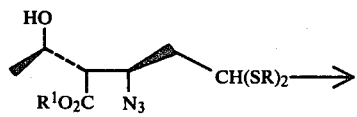
8

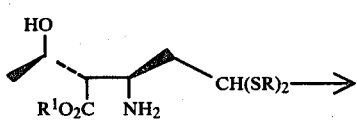
9

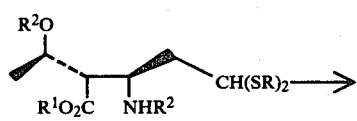
10

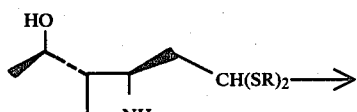
11

12

Diagram I is discussed below. In preface to Diagram I, however, it should be noted that thienamycin (V) is an exceptionally potent, broad spectrum β-lactam antibiotic, particularly notable for its activity against Pseudomonas sp. and its resistance to β-lactamases. The absolute stereochemistry of thienamycin (V)

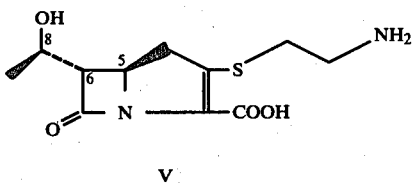
V

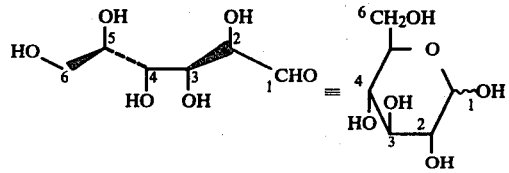
VI is 5R, 6S, 8R. The present invention comprises a chiral, total synthesis of thienamycin starting from the readily available sugar, D-glucose (dextrose) (VI). The 5R, 6S, 8R stereochemistry of thienamycin is inherent in the D-glucose structural symmetry, as depicted in VI (chiral centers 3, 4 and 5). D-glucose is functionalized to afford optically active azetidinone aldehyde IV, via intermediates I, II, and III. Compound IV, above, is known to be useful in the total synthesis of thienamycin.

A key intermediate in the conversion of D-glucose into azetidinone aldehyde IV is methyl 3-azido-2,3,6-trideoxy-α-D-arabino-hexopyranoside (I). Compound I is transformed into methyl 3-azido-4-C-cyano-2,3,4,6-tetradeoxy-α-D-arabino-hexopyranoside (II), which is then converted, as depicted in the diagram above, into the open amino ester dithioacetal III and subsequently into azetidinone aldehyde IV.

Methyl 3-azido-2,3,6-trideoxy-α-D-arabino-hexopyranoside 4) is obtained either from methyl 2,6-dideoxy-α-D-arabino-hexopyranoside (3) or from methyl α-D-glucopyranoside (12a), as represented by the following reaction diagrams, respectively:

(a.) 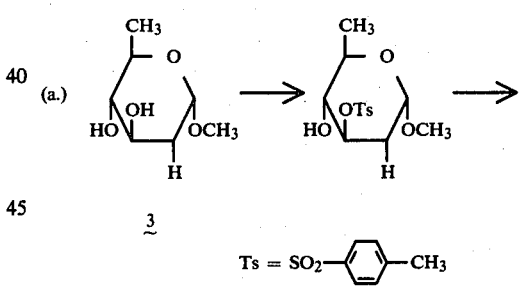
3

Ts = SO₂—⟨⟩—CH₃

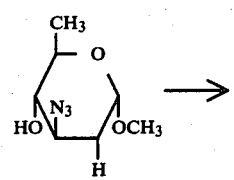
4

(b.) 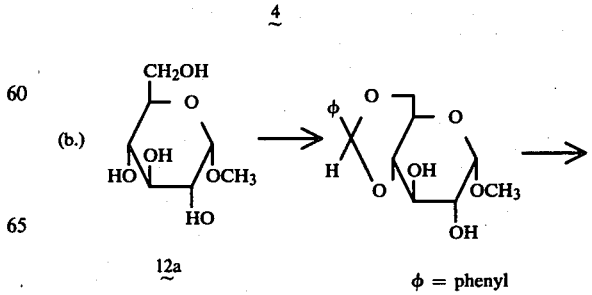
12a

φ = phenyl

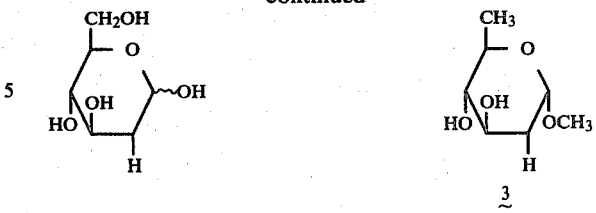

Methyl α-D-glucopyranoside (12) is obtained from D-glucose (1) as shown below,

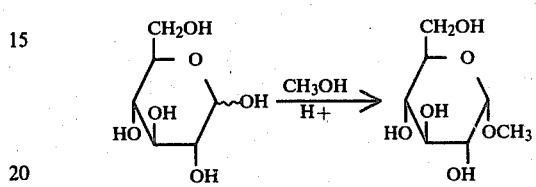

Now, returning to Diagram I, above, the transformation 1→2 is known. Typically D-glucose (1) is converted into methyl 2-deoxy-6O -D-glucopyranoside (2) by the following sequence of reactions: (a) acetic anhydride and pyridine or acetic anhydride and sodium acetate to give penta-O-acetyl-D-glucopyranose; (b) hydrogen bromide in acetic acid to afford tetra-O-acetyl-α-D-glucopyranosyl bromide; (c) zinc and acetic acid to yield tri-O-acetyl-D-glucal; (d) sodium (or sodium methoxide) in methanol to give D-glucal; and (e) methanolic hydrogen chloride to yield 2. Conversion of D-glucal (or 2-deoxy-D-glucose) into 2 is reported in I. W. Hughes, et. al., *J. Chem. Soc.*, 2846 (1949).

The transformation 2→3 is accomplished by treating 2 in a solvent such as toluene, benzene, dimethylformamide, dichloromethane, or the like with an iodinating agent (or other halogenating agent), such as methyltriphenoxyphosphonium iodide, iodotriphenoxyphosphonium iodide, triphenyphoshpine-N-iodosuccinimide; triphenylphosphine-tetraiodomethane; triphenylphosphine-2,4,5-triiodoimidazole; triphenylphosphine, iodine, and imidazole; or the like at a temperature of from 20° to 100° C. for from 1 to 24 hours.

The hydrogenolysis to yield compound 3 is typically conducted in a solvent, such as methanol, ethanol, ethyl acetate, or the like, at a temperature of from 20° to 50° C. in the presence of a catalyst such as Raney nickel, palladium-on-charcoal, palladium black, palladium hydroxide, or the like, under a hydrogen pressure of from 1 to 5 atmospheres.

Transformation 3→4 is accomplished in a solvent such as pyridine or dichloromethane, chloroform, or the like with p-toluenesulfonyl chloride, p-toluenesulfonic anhydride, or the like in the presence of a base such as Et₃N, iPr₂NEt, pyridine, 4-dimethylaminopyridine, or the like, at a temperature of from −15° C. to +10° C. for from 24 hours to 10 days to yield the C-3 tosylate, which upon treatment, in a solvent such as ethanol, methanol, or the like, with alcoholic base, such as ethanolic sodium hydroxide, ethanolic potassium hydroxide, methanolic sodium hydroxide, methanolic potassium hydroxide, or the like, followed by treatment with an alkali azide, such as lithium azide, sodium azide, potassium azide, or the like in the presence of ammonium chloride at a temperature of from 50° C. to 100° C. from 1 hour to 24 hours yields the azide 4.

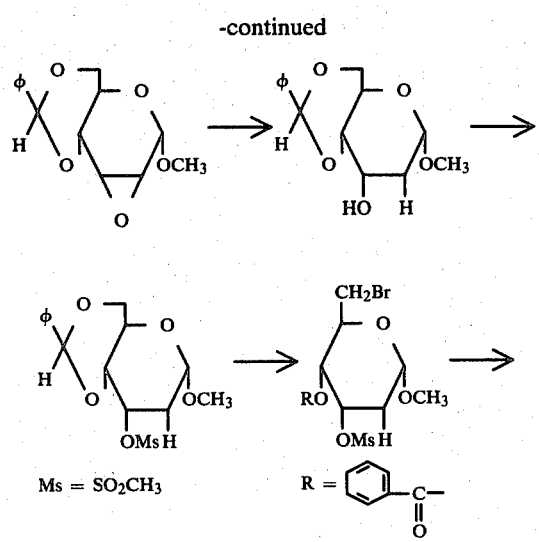

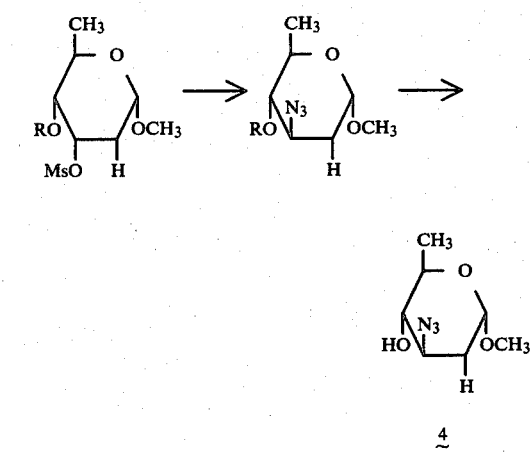

Methyl 2,6-dideoxy-α-D-arabino-hexopyranoside (3) is obtained from D-glucose (1), via 2-deoxy-D-glucose (13), or D-glucal (14), and methyl 2-deoxy-α-D-Glucopyranoside (2), as represented by the following reaction diagram:

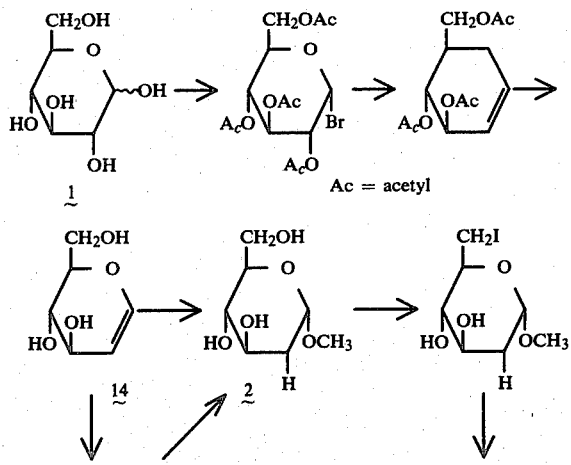

Treatment of 4 in a solvent such as dichloromethane, chloroform, or the like with trifluoromethanesulfonyl chloride, trifluoromethanesulfonic anhydride, or the like in the presence of a base such as Et₃N, iPr₂NEt, pyridine, 4-dimethylaminopyridine or the like at a temperature of from −76° C. to 0° C. for from 20 mintues to 2 hours, followed by treatment with a brominating agent, such as lithium bromide, sodium bromide, tetraethylammonium bromide, tetra-n-butylammonium bromide or the like in a solvent such as, dichloromethane, acetonitrile tetrahydrofuran, dimethylformamide, or the like at a temperature of from 20° C. to 100° C. for from 30 minutes to 5 hours, yields the 4-bromo-4-deoxy sugar 5 which upon treatment with sodium cyanide, potassium cyanide (in the presence or absence of a crown ether), tetraethylammonium cyanide, tetra-n-butylammonium cyanide, tetraethylammonium chloride-sodium cyanide, or the like in a solvent such as dichloromethane, acetonitrile, tetrahydrofuran, dimethylformamide, dimethylsulfoxide, hexamethylphosphoramide, or the like at a temperature of from 30° C. to 150° C. for from 15 minutes to 24 hours yields compound 6.

In words relative to the Diagram I, above, the transformation 6→7 is accomplished by treating 6 in a mineral acid such as hydrochloric acid, sulfuric acid, or the like with an alkanethiol having 1-6 carbon atoms, such as methanethiol, ethanethiol, propanethiol, or the like, or an alkanedithiol, such as 1,2,-ethanedithiol, 1,3-propanedithiol, or the like at a temperature of from 0° to 30° C. for from 30 min. to 24 hours. The value of R is determined by the identity of the thiol taken in reaction. Compound 6 is disclosed and claimed in previously incorporated by reference, concurrently filed U.S. Patent application Ser. No. 248,178. The preparation of 6 is given below.

Alcoholysis 7→8 is accomplished by treating 7 either (a) in an alcohol such as methanol, ethanol, propanol, or the like with an alkali alkoxide, such as sodium methoxide, sodium ethoxide, sodium propoxide, or the like, at a temperature of from 0° to 30° C. for from 1 to 24 hours, followed by neutralization with a cation-exchange resin in the H⁺cycle, such as Amberlite Ir-120(H⁺), Bio-Rad Ag 50W, Dowex 50W, or the like; or (b) in a solvent such as diethyl ether, dichloromethane, chloroform, or the like with an alcohol, such as methanol, ethanol, propanol or the like saturated at 0° C. with dry hydrogen chloride gas, at a temperature of from 0° to 30° C. for from 2 to 24 hours, followed by hydrolysis at 0° C. The value of $R^1$ is determined by the identity of the alcohol taken in reaction.

Conversion of azido ester 8 into amino ester 9 is accomplished by treating 8 in a solvent such as methanol, ethanol, ethyl acetate, or the like, at a temperature of from 20° to 50° C. in the presence of a catalyst such as palladium-on-charcoal, palladium black, palladium hydroxide, palladium-on-barium sulfate, platinum oxide or the like under a hydrogen pressure of from 1 to 5 atmospheres.

The transformation 9→10 establishes the protecting group $R^2$. The most preferred protecting groups $R^2$ are triorganosilyl groups such as t-butyldimethylsilyl, t-butyldiphenylsilyl, triphenylsilyl, isopropyldimethylsilyl, and the like. Typically, silylation is accomplished by treating 9 with the corresponding triorganosilyl chloride in a solvent such as dimethylformamide, hexamethylphosphoramide, acetonitrile, tetrahydrofuran, and the like at a temperature of from −20° to 80° C. for from 0.5 to 24 hours in the presence of a base such as triethylamine, diisopropylethylamine, or imidazole.

The resulting species 10 in a solvent such as ether, THF, DME, or the like is treated with EtMgBr, MeMgI, t-BuMgCl, or the like at a temperature of from −40° to 50° C. for from 1 to 72 hours to provide azetidinone 11.

The transformation 11→12 is accomplished by treating 11 in a solvent such as aqueous THF, aqueous acetone, aqueous acetonitrile, aqueous p-dioxane, or the like with a Lewis acid, such as mercuric oxide, mercuric chloride, boron trifluoride-etherate, thallium trinitrate, silver tetrafluoroborate, or the like at a temperature of from 0° to 50° C. for from 1 to 24 hours.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Step A: Preparation of 3-azido-4-C-cyano-2,3,4,6-tetradeoxy-D-arabino-hexose trimethylene dithioacetal

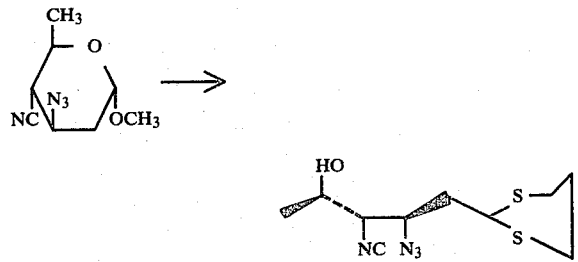

Methyl 3-azido-4-C-cyano-2,3,4,6-tetradeoxy-α-D-arabino-hexopyranoside (675 mg, 3.44 mmol) is treated with concentrated hydrochloric acid (150 ml) for 5 min at room temperature, at which time 1,3-propanedithiol (0.69 ml, 6.87 mmol) and sufficient methanol to achieve solution are added. After the reaction mixture is stirred for 1 hour at room temperature, the methanol is removed by evaporation under vacuum, and the product is extracted with dichloromethane. The combined organic extracts are evaporated under vacuum, and the residue is chromatographed on a column of silica gel (Merck No. 7734) (1:1 diethyl ether-hexane) to yield 890 mg (95%) of the trimethylene dithioacetal as a white crystalline solid; ¹H NMR (300 MHz, CDCL₃): 1.50 (d, C—CH₃), 1.76 (d, OH-5, $J_{OH, H-5}$ 5 Hz), 1.92 (m, 1H, dithiane H-4), 2.07 (septet, H-2), 2.17 (m, 1H, dithione H-4'), 2.27 (septet, H-2'), 2.68 (dd, H-4, $J_{3,4;\ 4,5}$ 3.2, 9 Hz), 2.84–3.00 (m, 4H, dithiane H-3's), 4.14–4.26 (m, 2H, H-1, H-5), 4.34 ppm (m, H-3)] mass spectrum m/e 272(M).

Step B:
3-Azido-4-C-carbomethoxy-2,3,4,6-tetradeoxy-D-arabino-hexose trimethylene dithioacetal

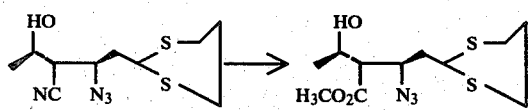

Dry hydrogen chloride gas is bubbled for 1 hour through a solution of 3-azido-4-C-cyano-2,3,4,6-tetradeoxy-D-arabino-hexose trimethylene dithioacetal (885 mg, 3.25 mmol) in diethyl ether (5 ml) and absolute methanol (5 ml) cooled in an ice-bath. The solution is then allowed to stand overnight at room temperature and evaporated under vacuum. The residue is taken up in dichloromethane, washed with saturated sodium hydrogen carbonate solution, and evaporated. the resulting material is chromatographed on a column of silica gel (Merck No. 7734) (10:1 diethyl ether:hexane) to afford 744 mg (75%) of the desired azido ester trimethylene dithioacetal; IR (CHCl₃):

1733 (C), 2095 (N₃); ¹H MNR (300 MHz, CDCl₃): 3.79 (s, 3H, CO₂CH₃).

Step C:
3-Amino-4-C-carbomethhoxy-2,3,4,6-tetradeoxy-D-arabino-hexose trimethylene dithioacetal

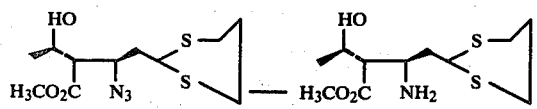

A mixture of 3-azido-4-C-carbomethoxy-2,3,4,6-tetradeoxy-D-arabino-hexose trimethylene dithioacetal (736 mg, 2.41 mmol) and 5% palladium-on-charcoal (300 mg) in methanol (20 ml) is hydrogenated at a pressure of 1 atmosphere for 5 hours at room temperature. The catalyst is then removed by filtration through Celite and the filtrate evaporated and dried in vacuo to give TLC-chromatographically- homogeneous, ninhydrin-positive amino ester trimethylene dithioacetal; yield 653 mg (97%);

IR (CHCl₃); 1733 (C=O); ¹H NMR (CDCl₃, 300 MHZ): 3.80 (s, 3H, CO₂CH₃).

Step D:
3α-[(1'R)-hydroxyethyl]-4β-[2',2'-(1,3-propanedithio)-ethyl]-2-azetidinone

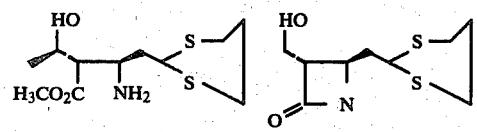

t-Butyldimethylchlorosilane (737 mg, 4.89 mmol) is added in one portion to a solution of 3-amino-4-C-carbomethoxy-2,3,4,6-tetradeoxy-D-arabino-hexose trimethylene dithioacetal (651 mg, 2.33 mmol) and triethylamine (0.68 ml, 4.89 mmol) in anhydrous dimethylformamide (10 ml) at 0° C. After 15 min at 0° C., the reaction mixture is stirred at room temperature for 24 hours. Most of the solvent is removed by evaporation under vacuum. The residue is partitioned between diethyl ether (75 ml) and water. The ethereal phase is washed with 2.5 N hydrochloric acid (15 ml), water (3×15 ml), and brine. The organic phase is dried (magnesium sulfate) and evaporated in vacuo to afford 3-(t-butyldimethylsilyl)-amino-4-C-carboxymethoxy-5-0-t-butyldimethylsilyl-2,3,4,6-tetra-deoxy-D-arabino-hexose trimethylene dithioacetal.

Anhydrous diethyl ether (6 ml) is added to the flask containing the disilyl derivative. The resulting solution is stirred under a nitrogen atmosphere with ice-bath cooling. Ethereal ethyl magnesium bromide (0.80 ml of a 2.94 M solution, 2.35 mmol) is added to 0° C., and the mixture is stirred overnight at room temperature. The mixture is then cooled in an ice-methanol bath while ammonium chloride-saturated 2N hydrochloric acid (2.5 ml) is slowly added with stirring. The resulting mixture is diluted with ethyl acetate (2.5 ml) and water (2.5 ml) and the layers are separated. The aqueous portion is extracted with more ethyl acetate (3×5 ml). The combined organic solution is washed with water (5 ml), 5% aqueous sodium bicarbonate solution (3 ml), water (3 ml), and brine, dried (magnesium sulfate), and filtered. The material obtained upon evaporation of the filtrate is purified by chromatography on silica gel (Merck No. 7734) to yield the desired 2-azetidinone trimethylene dithioacetal; yield 144 mg.

Step E: 3α-[(1'R)-hydroxyethyl]-4β-(2'-oxoethyl)-2-azetidinone

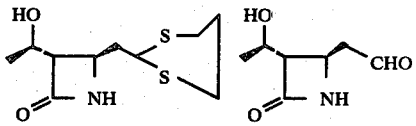

To a suspension of red mercuric oxide (3.5 equiv.) and boron trifluoride-etherate (3 equiv) in 17% aqueous acetone (3.5 ml) is added with stirring under nitrogen a solution of 3α-[(1'R)-hydroxyethyl]-4β-[2',2'-(propanedithio)-ethyl]-2-azetidinone (141 mg, 0.57 mmol) in tetrahydrofuran (1 ml). After stirring for 24 hours, water (1.5 ml) and acetone (3 ml) are added and the mixture neutralized with sodium bicarbonate. The precipitate is filtered, the filtrate concentrated and extracted several times with chloroform. The organic extracts are washed with brine, dried (magnesium sulfate), and evaporated in vacuo to afford 63 mg (70%) of the desired aldehyde azetidinone.

EXAMPLE 2

Process for preparing Methyl 3-azido-4-C-cyano-2,3,4,6-tetradeoxy-α-D-arabinohexopyranoside

STEP A

Methyl 2,6-dideoxy-3-O-(p-toluenesulfonyl)-α-D-arabinohexopyranoside

To a solution of methyl 2,6-dideoxy-α-D-arabinohexopyranoside (6.3 g, 38.8 mmol) in pyridine (200 ml)

at 0° C. is added freshly recrystallized p-toluenesulfonyl chloride (7.6 g, 39.9 mmol). The mixture is kept 5 days at 0° C., at which time additional p-toluenesulfonyl chloride (1.9 g) is added. After 3 days at 5° C., the mixture is poured into ice-water, extracted several times with dichloromethane, the combined organic extracts evaporated under vacuum, coevaporated several times with toluene, and chromatographed on silica gel (Merck No. 7734) (1:2 diethyl ether-petroleum ether, b.p. 35°–60° C.) to yield 8.5 g (69%) of the product as a solid; $^1$H NMR (300 MHz, CDCl$_3$): 1.30 (d, C-CH$_3$), 1.83 (td, H-2ax, J-H-1, H-2ax, 3.5 Hz, J H2eq, H2ax 12.8 Hz), 2.09 (m, H-2eq, J H-1, H-2eq 1.1 Hz, J H-2eq, H-3 5.5 Hz), 2.46 (s, ArCH$_3$), 2.53 (d, O$\underline{H}$), 3.27 (s, OCH$_3$), 3.32 (td, H-4, $J_{H\text{-}4,H\text{-}5}=J_{H\text{-}4, H\text{-}3}=8.8$ Hz), 3.65 (m, H-5), 4.68 (broad d, H-1), 4.74 (ddd, H-3), 7.38 (d, 2H, Ar), 7.85 ppm (d, 2H, AR); mass spectrum m/e 285 (M-OCH$_3$), 272 (M-CH$_3$CHO).

Anal. C, H, S.

STEP B

Methyl 3-Azido-2,3,6-tredeoxy-α-D-arabino-hexopyranoside

To a solution of methyl 2,6-dideoxy-3-O-(p-toluenesulfonyl)-α-D-arabino-hexopyranoside (8.4 g, 26.6 mmol) in absolute ethanol (80 ml) is added phenolphthalein (as an indicator) and subsequently dropwise at 60° C. saturated ethanolic sodium hydroxide until color persists for ≈10 minutes. The reaction mixture is then cooled to 10° C., the precipitated sodium tosylate removed by filtration, the filtrate brought to pH 7 with 2 N hydrochloric acid. Sodium azide (4.9 g) and ammonium chloride (2.9 g) are then added, and the mixture is stirred overnight at reflux temperature. After concentration, the residue is partitioned between dichloromethane and water, the aqueous layer extracted with dichloromethane, the combined organic extracts evaporated under vacuum, and chromatographed on silica gel (Merck No. 7734) (30:1 chloroform-ethyl acetate) to afford the pure product as a colorless syrup; yield 3.7 g (74%); $^1$HNMR (300 MHz, CDCl$_3$): 1.30 (d, C—CH$_3$), 1.73 (td, H-2ax, $J_{H\text{-}1,H\text{-}2ax}$3.6 Hz), 2.17 (m, H-2eq, $J_{h\text{-}1, H\text{-}2eq}$ 1.2 Hz, $J_{H\text{-}2eq, H\text{-}3}$ 5 HZ), 3.14 (t, H-4, $J_{H\text{-}3, H\text{-}4}=J_{H\text{-}4, H\text{-}5}=9$ Hz), 3.34 (s, OCH$_3$), 3.63–3.79 (m, H-3,5), 4.75 (broad d, H-1); mass spectrum m/e 187 (M), 156 (M—OCH$_3$), 145 (M—N$_3$), 143 (M—CH$_3$CHO).

STEP C

Methyl 3-azido-4-bromo-2,3,4,6-tetradeoxy-α-D-lyxohexopyranoside

To a solution of methyl 3-azido-2,3,6-trideoxy-α-D-arabino-hexopyranoside (3.6 g, 19.2 mmol) in dichloromethane (100 ml) cooled in an ice-bath are added pyridine (2 ml) and dropwise a solution of trifluoromethanesulfonic anhydride (3.2 ml, 19.0 mmol) in dichloromethane (25 ml). After stirring for 10 minutes at 0° C. with exclusion of moisture, additional pyridine (2 ml) and trifluoromethanesulfonic anhydride (2.6 ml) are added. After 10 minutes at 0° C., the reaction mixture is diluted with dichloromethane (130 ml) and poured into a separatory funnel containing ice-water. The organic layer is separated and washed with cold N hydrochloric acid, saturated sodium hydrogen-carbonate, water, and dried (sodium sulfate). Evaporation under vacuum gives the 4-trifluoromethane-sulfonate that is dissolved in dry acetonitrile (50 ml) and treated with tetra-n-butylammonium bromide (12.7 g, 39.4 mmol) for 1 hour at 40° C. The reaction mixture is concentrated, the residue partitioned between dichloromethane and water, the organic layer evaporated under vacuum and the resulting syrup chromatographed on a column of silica gel (Merck No. 7734) (1:2 dichloromethane-hexane) to yield 3.65 g (76%) of the bromide; $^1$H NMR (300 MHz, CDCl$_3$): 1.32 (d, C—CH$_3$), 1.90 (dd, H-2eq), 2.20 (td, H-2ax), 3.36 (s, OCH$_3$), 3.84–4.00 (m, H-3,5), 4.27 (d, H-4), 4.86 ppm (d, H-1); mass spectrum m/e 250 (M).

STEP D

Methyl 3-azido-4-C-cyano-2,3,4,6-tetradeoxy -α-D-arabino-hexopyranoside

To a solution of methyl 3-azido-4-bromo-2,3,4,6-tetradeoxy-α-D-lyxo-hexopyranoside (3.5 g, 14.0 mmol) in freshly distilled acetonitrile (75 ml) is added tetra-n-butylammonium cyanide (7.5 g, 28.0 mmol). The reaction mixture is stirred for 1 hour at 50° C., cooled, partially concentrated (25 ml), diluted with dichloromethane (250 ml), washed with water (3X), dried (sodium sulfate), and evaporated under vacuum. The residue is chromatographed on a column of silica gel (Merck No. 7734) (1:10 diethyl ether-hexane) to yield 687 mg (25%) of the desired cyanide as a colorless syrup; $^1$H NMR (300 MHz, CDCl$_3$): 1.42 (d, C—CH$_3$), 1.60 td, H-2ax, $J_{H\text{-}1,H\text{-}2ax}$ 3.5 Hz), 2.21 (m, H-2eq, $J_{H\text{-}1, H\text{-}2eq}$ 1.2 Hz, $J_{H\text{-}2eq, H\text{-}3}$5 Hz), 2.26 (t, H-4, $J_{H\text{-}3, H\text{-}4}=J_{H\text{-}4, H\text{-}5}=10.8$ Hz), 3.36 (s, OCH$_3$), 3.92–4.06 (m, H-3,5), 4.85 (broad d, H-1); mass spectrum m/e 165 (M-OCH$_3$), 154 (M-N$_3$), 152 (M-CH$_3$CHO).

What is claimed is:

1. A process for preparing:

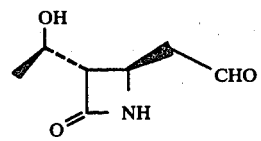

comprising the steps of: treating:

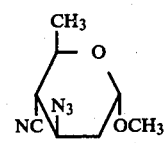

with mineral acid and an alkanethiol, a phenylalkanethiol, or a alkanedithiol to yield:

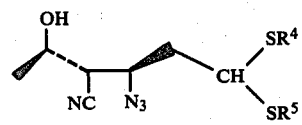

followed by alcoholysis with the alcohol R$^1$OH to yield

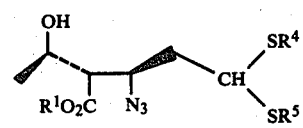

wherein R¹ is alkyl having 1-6 carbon atoms; followed by treating with hydrogen and a hydrogenation catalyst to yield:

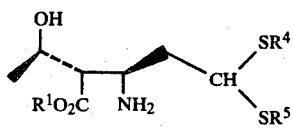

followed by treating with a triorganosilyl chloride and cyclization in the presence of a Grignard reagent selected from ethylmagnesiumbromide, methyl magnesiumiodide and t-butylmagnesiumchloride, to yield

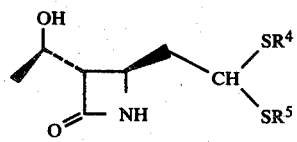

followed by treating in a solvent selected from aqueous tetrahydrofuran, aqueous acetone, aqueous acetonitrite and aqueous p-dioxane with a Lewis acid selected from mercuric oxide, mercuric chloride, boron trifluoride etherate, thallium trinitrate and silver tetrafluorobovate wherein $R^4$ and $R^5$ are independently selected from alkyl having 1-6 carbon atoms, phenylalkyl; or wherein the $SR^4$ and $SR^5$ groups taken together with the carbon atom to which they are attached form a dithiacycloalkyl group.

2. A process according to claim 1, wherein $SR^4$ and $SR^5$ are joined to form $-S-(CH_2)_3-S-$.

* * * * *